United States Patent
Yang (10) Patent No.: US 10,016,557 B2
(45) Date of Patent: Jul. 10, 2018

(54) SAFETY MEDICAL CONNECTOR (71) Applicant: Sunder Biomedical Tech. Co., Ltd., Taichung (TW)

(72) Inventor: Chao-Chin Yang, Kaohsiung (TW)

(73) Assignee: Sunder Biomedical Tech. Co., Ltd., Taichung (TW)

( * ) Notice: Subject to any disclaimer, the term of this patent is extended or adjusted under 35 U.S.C. 154(b) by 80 days.

(21) Appl. No.: 15/277,210

(22) Filed: Sep. 27, 2016

(65) Prior Publication Data

US 2018/0036479 A1 Feb. 8, 2018

(30) Foreign Application Priority Data

Aug. 8, 2016 (TW) .............................. 105125110 A (51) Int. Cl.
*A61M 5/158* (2006.01)
*A61M 39/10* (2006.01)

(52) U.S. Cl.
CPC ........ *A61M 5/158* (2013.01); *A61M 39/1011* (2013.01)

(58) Field of Classification Search
CPC .......................... A61M 5/158; A61M 39/1011
See application file for complete search history.

(56) References Cited

U.S. PATENT DOCUMENTS

| | | | | |
|---|---|---|---|---|
| 2008/0108944 A1* | 5/2008 | Woehr | ................. | A61B 5/1411 604/164.08 |
| 2008/0287920 A1* | 11/2008 | Fangrow | ............ | A61M 39/1011 604/535 |
| 2010/0004634 A1* | 1/2010 | Whitley | ............. | A61M 39/1011 604/537 |
| 2010/0249723 A1* | 9/2010 | Fangrow, Jr. | ......... | A61M 39/24 604/247 |
| 2012/0192968 A1* | 8/2012 | Bonnal | .............. | A61M 39/1011 137/454.2 |
| 2013/0079730 A1* | 3/2013 | Mosler | .................. | A61M 39/10 604/244 |
| 2014/0246616 A1* | 9/2014 | Fangrow | ............... | A61M 39/26 251/148 |
| 2014/0330203 A1* | 11/2014 | McLoughlin | ........... | A61M 5/20 604/131 |
| 2015/0265499 A1* | 9/2015 | Takeuchi | .............. | A61M 5/162 604/414 |

FOREIGN PATENT DOCUMENTS

TW          I378806          1/2011

* cited by examiner

*Primary Examiner* — James M Hewitt, II (74) *Attorney, Agent, or Firm* — Muncy, Geissler, Olds & Lowe, P.C.

(57) ABSTRACT

A safety medical connector includes a composite inner pipe, a first resilient element, and a second resilient element. The first resilient element hermetically seals the entrance of the composite inner pipe. In operation, the first resilient element is pushed aside such that the entrance of the inner pipe opens. After use, the second resilient element drives the composite inner pipe and the first resilient element to restore position. Hence, the safety medical connector advantageously features reduced liquid residue and enhanced structural stability.

10 Claims, 7 Drawing Sheets

SAFETY MEDICAL CONNECTOR

BACKGROUND OF THE INVENTION

Field of the Invention

The present invention relates to a medical equipment, more particularly to a safety medical connector which dispenses with sharp needles.

Description of the Prior Art

Medical treatment usually entails injecting into and drawing various liquids from patients with various infusion pipelines, for example, in intravenous fluid infusion, medication administration, and blood drawing. In this regard, an infusion connector connects with various infusion pipelines and thus functions as a valve of liquid input or output. In particular, with increasingly great importance being attached to medical professionals' safety, safety medical connectors which dispense with sharp needles are already in use by plenty medical institutions.

However, a conventional safety medical connector has therein considerable gaps which keep residues of a liquid or medication after an infusion is done. The next infusion may cause the residual liquid or medication to mix with an incoming liquid, posing a risk of bacterial infections. Hence, there is a need to provide a safety medical connector capable of reducing residues.

Taiwan patent I378806 discloses a safety medical connector capable of reducing residues, comprising a housing, a resilient valve, and a bidirectional communication component. The housing has two openings. The resilient valve is received in the housing and hermetically seals the two openings. The resilient valve defines a receiving space for holding the bidirectional communication component. The bidirectional communication component has therein an infusion channel. The operation mechanism of the safety medical connector is as follows: when pushed by an external connector, the resilient valve is deformed to thereby not only allow the bidirectional communication component to stretch the resilient valve open but also enable the infusion channel to communicate with the two openings. Upon completion of the operation, a trace of the liquid remains in the infusion channel instead of between the housing and the resilient valve.

Although the aforesaid conventional safety medical connector solves the problem with liquid residues, a new problem arises because the bidirectional communication component is supported and positioned only by the resilient valve. The resilient valve must be pushed and deformed whenever to work; hence, the resilient valve is anticipated to lose its resilience after long use and thus dislocate the bidirectional communication component, thereby causing a leak.

Therefore, the conventional safety medical connectors still have room for improvement.

SUMMARY OF THE INVENTION

It is an objective of the present invention to provide a safety medical connector with reduced liquid residue and enhanced structural stability.

In order to achieve the above and other objectives, the present invention provides a safety medical connector which comprises a first inner pipe, a second inner pipe, a housing, a first resilient element, and a second resilient element. The first inner pipe has a first protruding portion, a fitting portion, and at least a first abutting portion. The first protruding portion and the first abutting portion are connected to the fitting portion. The free end of the first protruding portion has at least a first through hole. The first protruding portion has therein a first passage. The first through hole is in communication with the first passage. The second inner pipe has a second protruding portion, a trunk portion, and at least a second abutting portion. The second protruding portion and the second abutting portion are connected to the trunk portion. The free end of the second protruding portion has at least a second through hole. The second protruding portion and the trunk portion has therein a second passage. The second through hole is in communication with the second passage. The fitting portion and the trunk portion fit each other. The first abutting portion and the second abutting portion alternate each other. The free end of the first protruding portion and the free end of the second protruding portion point in two opposite directions, respectively. The first passage is in communication with the second passage. The housing has a peripheral wall as well as a first end wall and a second end wall which close the two ends of the peripheral wall, respectively. The peripheral wall, the first end wall, and the second end wall jointly define a first receiving space. The first end wall and the second end wall each have an opening whose rim extends outward to form a first circumferential wall and a second circumferential wall. The first circumferential wall defines a first channel. The second circumferential wall defines a second channel. The first resilient element has a head portion and a body portion. The head portion extends laterally from the body portion and forms a closed end. The other side of the body portion extends to form an opening end. The body portion has therein a second receiving space. The second receiving space is in communication with the opening end. The second resilient element has a first fixing portion, a second fixing portion and at least a connecting portion for connecting the first fixing portion and the second fixing portion. The first fixing portion is disposed at the housing. The second fixing portion is disposed at the second inner pipe. The first protruding portion points at the first circumferential wall. The first resilient element fits around the first protruding portion such that the first protruding portion penetrates the opening end and thus gets received in the second receiving space. The body portion of the first resilient element abuts against the second abutting portion. The head portion of the first resilient element is disposed inside the first circumferential wall to hermetically seal the first channel. The first abutting portion abuts against the second end wall, and the at least second through hole of the second protruding portion is received in the second channel, allowing the first passage and the second passage to be in communication with the second channel.

The safety medical connector disclosed in a preferred embodiment of the present invention further comprises a sealing element. The sealing element is attached to the second end wall and abutted against by the first abutting portion. The sealing element has a third through hole penetrable by the second protruding portion.

Regarding the safety medical connector disclosed in a preferred embodiment of the present invention, the sealing element has two opposing parallel surfaces, one said surface attached to an inner wall surface of the second end wall, and another said surface being abutted against by the first abutting portion.

Regarding the safety medical connector disclosed in a preferred embodiment of the present invention, the peripheral wall has at least a slit, and the first fixing portion of the second resilient element fits around an outer wall surface of the peripheral wall, allowing the connecting portion to be penetratingly disposed at the slit.

Regarding the safety medical connector disclosed in a preferred embodiment of the present invention, the first inner pipe has two opposing first abutting portions, and the second inner pipe has two opposing second abutting portions.

Regarding the safety medical connector disclosed in a preferred embodiment of the present invention, the free end of the first protruding portion is tapered and has a first lateral surface, the first through hole disposed on the first lateral surface.

Regarding the safety medical connector disclosed in a preferred embodiment of the present invention, the free end of the second protruding portion is tapered and has a second lateral surface, the second through hole disposed on the second lateral surface.

Regarding the safety medical connector disclosed in a preferred embodiment of the present invention, a neck portion is disposed at a junction of the head portion and the body portion of the first resilient element, and a pressing portion is disposed at a junction of the first end wall and the first circumferential wall, the pressing portion pressing against the neck portion.

Regarding the safety medical connector disclosed in a preferred embodiment of the present invention, a positioning notch is disposed at the body portion of the first resilient element, and a flange is disposed at the second abutting portion, the flange engaged with the positioning notch.

Regarding the safety medical connector disclosed in a preferred embodiment of the present invention, a resilient ring is disposed between the fitting portion of the first inner pipe and the trunk portion of the second inner pipe.

Accordingly, the safety medical connector of the present invention is effective in reducing liquid residues, because traces of used liquids are confined to the first passage and the second passage. Furthermore, the first abutting portion of the first inner pipe abuts against the second end wall of the housing, and thus the first inner pipe need not be supported by any other component, thereby enhancing structural stability even after long use.

Features of the present invention are described in detail later. However, persons skilled in the art understand that the detailed description and specific embodiments descriptive of the present invention are illustrative of the present invention rather than restrictive of the scope of the claims of the present invention.

DETAILED DESCRIPTION OF THE EMBODIMENT OF THE INVENTION

Referring to FIG. 1 through FIG. 4, the present invention provides a safety medical connector 10 which comprises a first inner pipe 20, a second inner pipe 30, a housing 40, a first resilient element 50, a second resilient element 60, and a sealing element 70.

Figure 4:
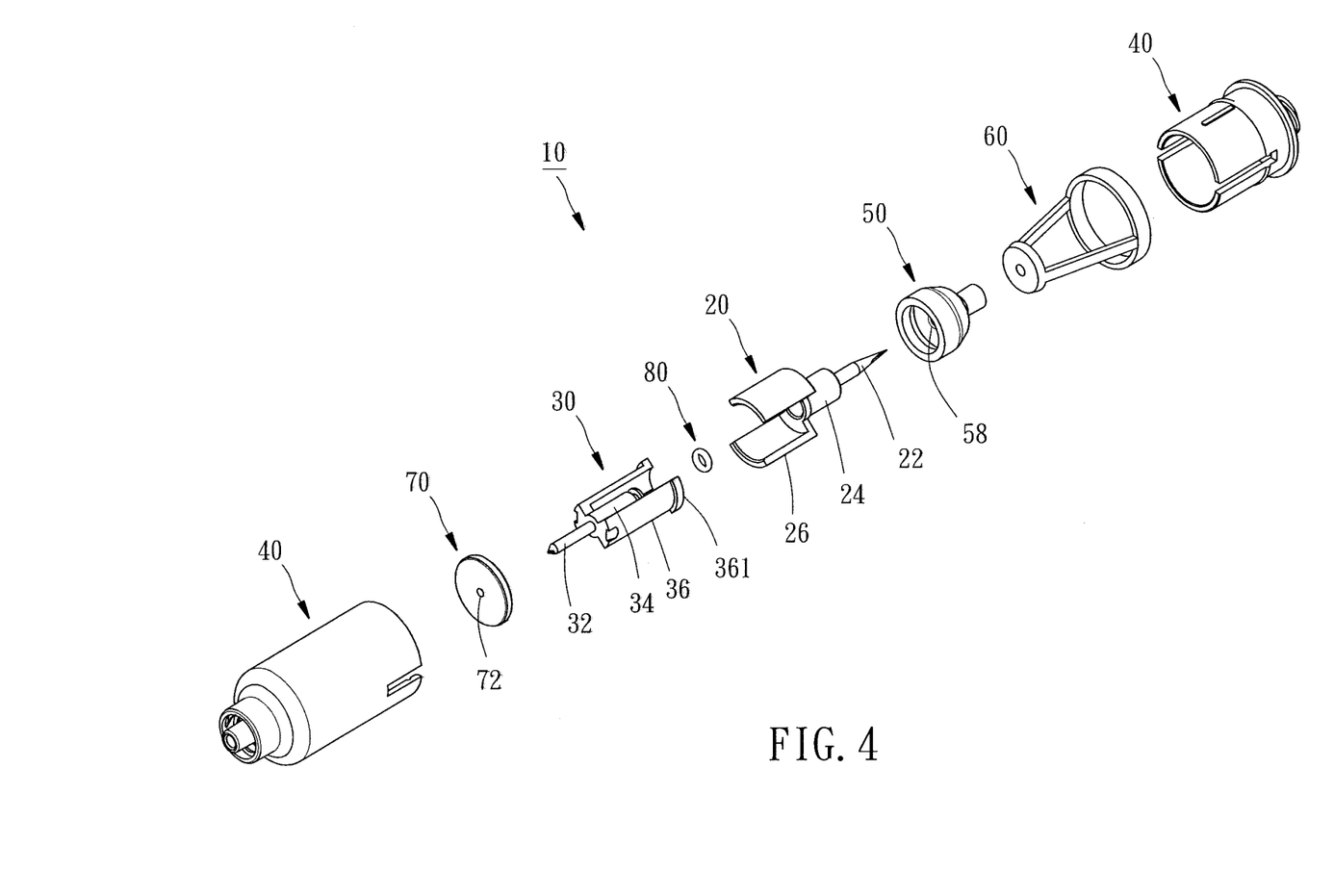
FIG. 4 is another exploded view of the present invention.
Figure 5:
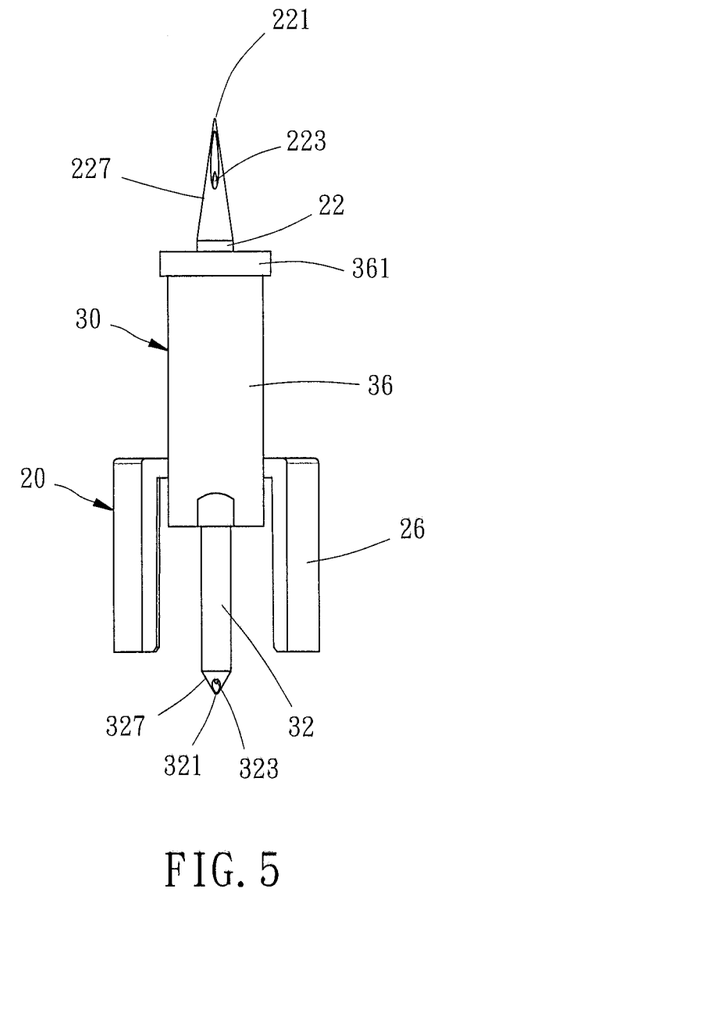
FIG. 5 is a partial lateral view of the present invention.

Referring to FIGS. 4, 5, the first inner pipe 20 has a first protruding portion 22, a fitting portion 24, and two first abutting portions 26. The fitting portion 24 is substantially hollow-core and cylindrical. The fitting portion 24 has one end connected to the first protruding portion 22. The fitting portion 24 has the other end connected to the two first abutting portions 26 in a manner that the two first abutting portions 26 are disposed at two opposite points at the other end of the fitting portion 24, respectively. The first protruding portion 22 has a free end 221 which points away from the fitting portion 24. The free end 221 of the first protruding portion 22 has two first through holes 223. The first protruding portion 22 has therein a first passage 225. The first through holes 223 are in communication with the first passage 225. In a variant embodiment, the first abutting portions 26 are in the number of one, and so are the first through holes 223.

The second inner pipe 30 has a second protruding portion 32, a trunk portion 34, and two second abutting portions 36. The second protruding portion 32 has one end connected to the trunk portion 34. The other end of the second protruding portion 32 is defined as a free end 321. The two second abutting portions 36 oppose each other and connect with the trunk portion 34. The free end 321 of the second protruding portion 32 has two second through holes 323. The second protruding portion 32 and the trunk portion 34 have therein a second passage 325. The second through holes 323 are in communication with the second passage 325. In a variant embodiment, the second abutting portions 36 are in the number of one, and so are the second through holes 323.

Figure 6:
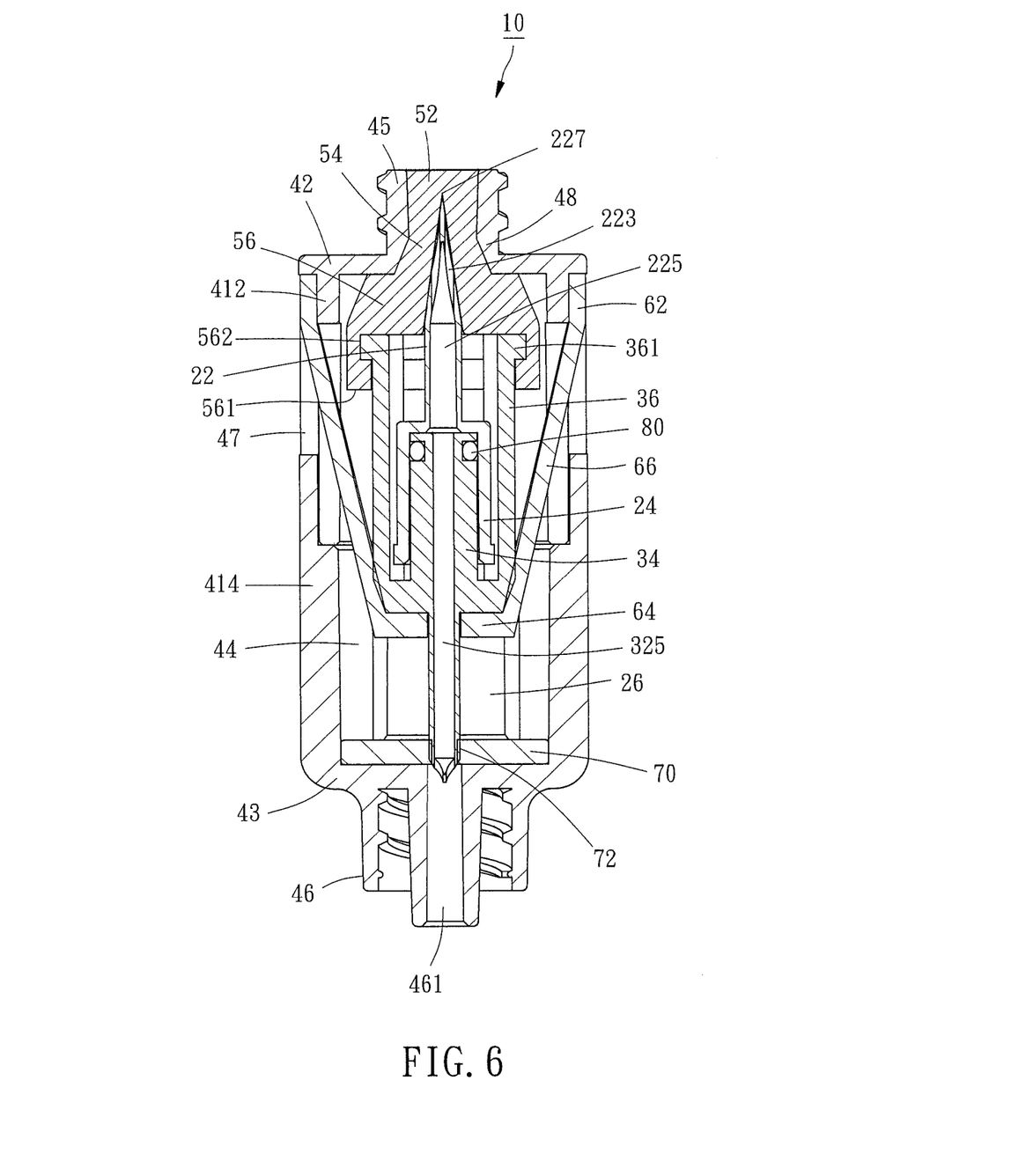
FIG. 6 is a cross-sectional view of the present invention taken along line 6-6 of FIG. 1.

The first inner pipe 20 and the second inner pipe 30 are put together in a manner described below. The fitting portion 24 of the first inner pipe 20 and the trunk portion 34 of the second inner pipe 30 fit each other. The first abutting portions 26 and the second abutting portion 36 alternate each other. The free end 221 of the first protruding portion 22 and the free end 321 of the second protruding portion 32 point in two opposite directions. Referring to FIG. 6, the first passage 225 is in communication with the second passage 325.

Figure 1:
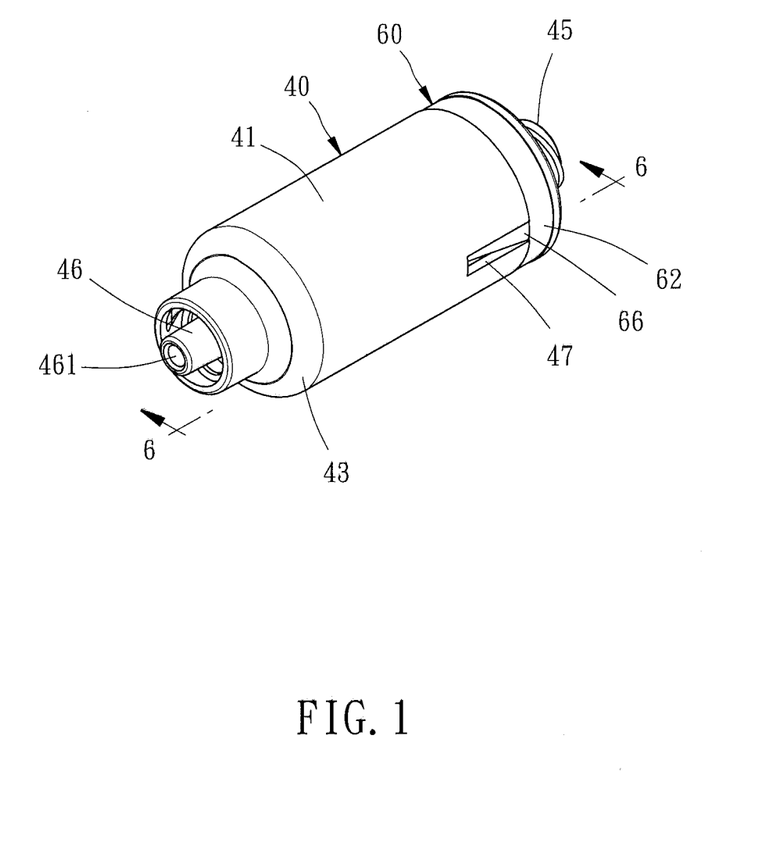
FIG. 1 is a perspective view of housing the present invention.
Figure 2:
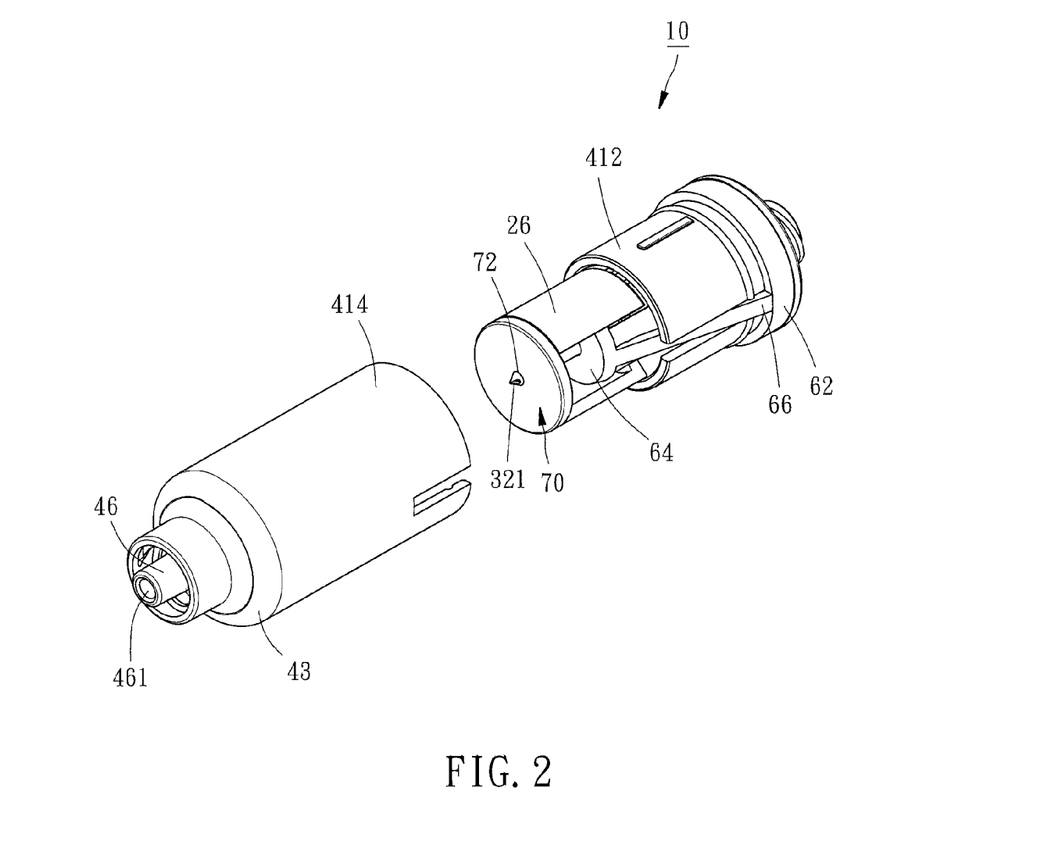
FIG. 2 is an exploded view of the present invention.
Figure 3:
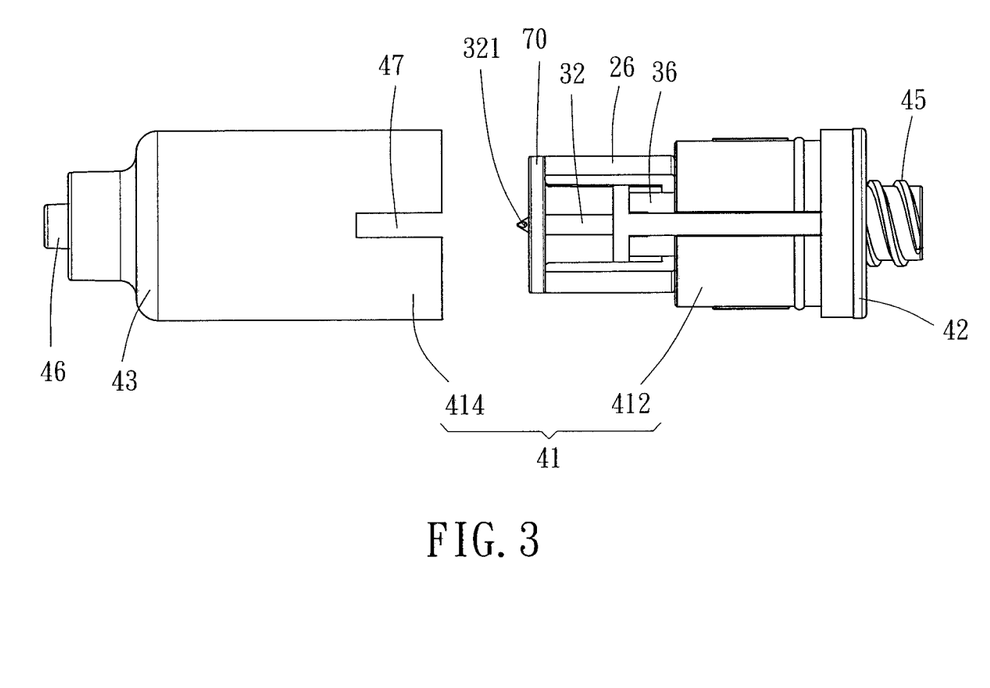
FIG. 3 is a lateral view of FIG. 2.
Figure 7:
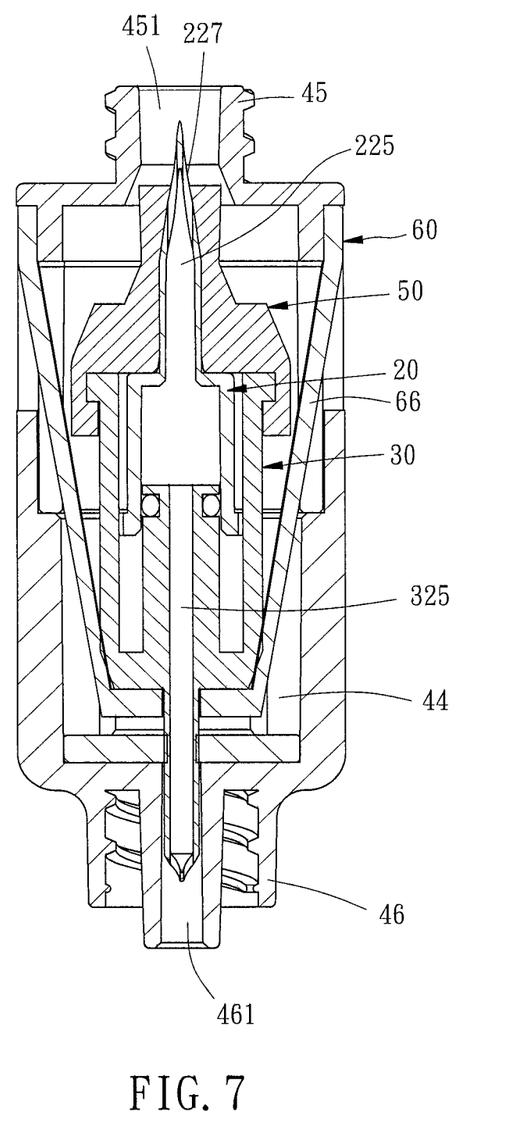
FIG. 7 is a schematic view of circulation within the present invention with reference to FIG. 6.

Referring to FIGS. 2, 3, the housing 40 has a peripheral wall 41 as well as a first end wall 42 and a second end wall 43 which close the two ends of the peripheral wall 41, respectively. In this preferred embodiment, to make assembly easy, the peripheral wall 41 has an inner peripheral wall 412 and an outer peripheral wall 414 which are engaged with each other. The inner peripheral wall 412 is connected to the first end wall 42. The outer peripheral wall 414 is connected to the second end wall 43. Referring to FIGS. 6, 7, the peripheral wall 41, the first end wall 42, and the second end wall 43 jointly define a first receiving space 44. The first end wall 42 and the second end wall 43 each have an opening whose rim extends outward to form a first circumferential wall 45 and a second circumferential wall 46. The first circumferential wall 45 defines a first channel 451. The second circumferential wall 46 defines a second channel 461. The first channel 451 and the second channel 461 have a smaller inner diameter than the peripheral wall 41. The peripheral wall 41 has two slits 47.

The first resilient element 50 has a head portion 52 and a body portion 56. The head portion 52 extends laterally from the body portion 56 and forms a closed end. The other side of the body portion 56 extends to form an opening end 561.

The body portion 56 has therein a second receiving space 58. The second receiving space 58 is in communication with the opening end 561.

The second resilient element 60 has a first fixing portion 62, a second fixing portion 64, and two connecting portions 66 connected to the first fixing portion 62 and the second fixing portion 64. The first fixing portion 62 fits around an outer wall surface of the peripheral wall 41. The second fixing portion 64 is disposed on an outer wall surface of the second protruding portion 32 of the second inner pipe 30. The connecting portions 66 are stretchably, penetratingly disposed at the slits 47. A variant embodiment is characterized by one said connecting portion 66, the first fixing portion 62 disposed at the other point on the peripheral wall 41, and the second fixing portion 64 disposed at the other point on the second inner pipe 30, wherein the slits 47 are dispensed with.

Referring to FIGS. 2, 6, 7, the sealing element 70 looks like a sheet and thus has two opposing parallel surfaces. One of the surfaces is attached to an inner wall surface of the second end wall 43. The first abutting portions 26 abut against the other surface. The sealing element 70 has a third through hole 72.

Referring to FIGS. 6, 7, the process of assembling the safety medical connector 10 is described below. The first protruding portion 22 points at the first circumferential wall 45. The first resilient element 50 fits around the first protruding portion 22 such that the first protruding portion 22 penetrates the opening end 561 and thus gets received in the second receiving space 58. The body portion 56 of the first resilient element 50 abuts against the second abutting portion 36. The head portion 52 of the first resilient element 50 is disposed inside the first circumferential wall 45 to hermetically seal the first channel 451.

The first abutting portions 26 abut against the sealing element 70 and the second end wall 43. The second protruding portion 32 penetrates the third through hole 72. The second through holes 323 are received in the second channel 461. The first passage 225 and the second passage 325 are in communication with the second channel 461. In this preferred embodiment, the free end 321 of the second protruding portion 32 is tapered and has a second lateral surface 327, and the second through holes 323 are disposed on the second lateral surface 327.

The operation of the safety medical connector 10 is described below.

Referring to FIGS. 6, 7, to perform infusion with the safety medical connector 10, the user inserts a syringe tip (not shown) into the first circumferential wall 45, and then the first resilient element 50 drives the second inner pipe 30 to move toward the second circumferential wall 46; meanwhile, the first through holes 223 of the first inner pipe 20 are no longer hidden by the first resilient element 50, and the syringe is in communication with the first passage 225, second passage 325, and second channel 461, thereby allowing the user to inject or withdraw a liquid. The two connecting portions 66 of the second resilient element 60 are stretched.

In the course of infusion, only the second inner pipe 30 is pushed and moved, but the first abutting portions 26 of the first inner pipe 20 abut against the second end wall 43 and thus remain unmoved, thereby enhancing structural stability. Furthermore, the liquid flows between the first passage 225, second passage 325, and the second channel 461 rather than seeps into the first receiving space 44, thereby reducing the residue of the liquid. Since the sealing element 70 hermetically seals a gap between the second protruding portion 32 and the second end wall 43, the gap is not predisposed to leakage. In a variant embodiment, the sealing element 70 does not necessarily look like a sheet; instead, the sealing element 70 is attached to the second end wall 43, and the first abutting portions 26 abut against the sealing element 70; hence, the safety medical connector 10 can achieve the objective of the present invention even when dispensed with the sealing element 70; meanwhile, the second through holes 323 of the second protruding portion 32 are directly received in the second channel 461, whereas the first passage 225 and the second passage 325 are in communication with the second channel 461.

To terminate the infusion process, the user takes the syringe tip out of the first circumferential wall 45 such that the second inner pipe 30 is guided by the stretched connecting portions 66 toward the first circumferential wall 45 to restore its position, whereas the first resilient element 50 is driven by the second abutting portion 36 to restore its position. As a result, the head portion 52 of the first resilient element 50 hermetically seals the first channel 451 again.

To enhance leakproofing, the first resilient element 50 further has a neck portion 54 for connecting the head portion 52 and the body portion 56. The outer diameter and inner diameter of the neck portion 54 increase gradually in the direction from the head portion 52 to the body portion 56. The free end 221 of the first protruding portion 22 is tapered and has a first lateral surface 227. The first through holes 223 are disposed on the first lateral surface 227. A pressing portion 48 is disposed at the junction of the first end wall 42 and the first circumferential wall 45. The pressing portion 48, the neck portion 54, and the first lateral surface 227 match each other to enable the pressing portion 48 to press against the neck portion 54 and the first lateral surface 227, thereby enhancing the hermetic sealing of the first through holes 223. The free end 321 of the second protruding portion 32 is tapered and has a second lateral surface 327. The second through holes 323 are disposed on the second lateral surface 327.

To enhance structural stability, a resilient ring 80 is disposed between the fitting portion 24 of the first inner pipe 20 and the trunk portion 34 of the second inner pipe 30 such that the first passage 225 and the second passage 325 are tightly connected.

To facilitate the dynamic interaction between the first resilient element 50 and the second inner pipe 30, a positioning notch 562 is disposed at the body portion 56 of the first resilient element 50, and a flange 361 is disposed at the free end of the second abutting portion 36, allowing the flange 361 to be engaged with the positioning notch 562.

The above detailed description, which is supported by drawings, is merely intended to provide an embodiment illustrative of the technical content and features of the present invention. The appended claims shall cover simple modifications, replacements or component reduction made, without going against the spirit embodied in the present invention, by persons skilled in the art after gaining insight into the technical content and features of the present invention.

What is claimed is:
1. A safety medical connector comprising:
a first inner pipe having a first protruding portion, a fitting portion, and at least a first abutting portion, with the fitting portion connected to the first protruding portion and the first abutting portion, at least a first through hole disposed at a free end of the first protruding portion, and a first passage disposed in the first protruding portion and being in communication with the first through hole;

a second inner pipe having a second protruding portion, a trunk portion, and at least a second abutting portion respectively, with the trunk portion connected to the second protruding portion and the second abutting portion, at least a second through hole disposed at a free end of the second protruding portion, a second passage disposed in the second protruding portion and the trunk portion, and the second through hole being in communication with the second passage, wherein the fitting portion and the trunk portion fit each other, the first abutting portion and the second abutting portion alternate with each other so as to interdigitate, the free end of the first protruding portion and the free end of the second protruding portion point in two opposite directions, and the first passage is in communication with the second passage, a housing having a peripheral wall and a first end wall and a second end wall which close two ends of the peripheral wall, respectively, allowing the peripheral wall, the first end wall, and the second end wall to jointly define a first receiving space, wherein the first end wall and the second end wall each have an opening whose rim extends outward to form a first circumferential wall and a second circumferential wall, the first circumferential wall defines a first channel, and the second circumferential wall defines a second channel;

a first resilient element having a head portion and a body portion, with the head portion extending laterally from the body portion and forming a closed end, wherein another side of the body portion extends to form an opening end, a second receiving space defined in the body portion and being in communication with the opening end; and a second resilient element having a first fixing portion, a second fixing portion, and at least a connecting portion for connecting the first fixing portion and the second fixing portion, with the first fixing portion disposed at the housing, and the second fixing portion disposed at the second inner pipe, wherein the first protruding portion points at the first circumferential wall, and the first resilient element fits around the first protruding portion such that the first protruding portion penetrates the opening end and thus gets received in the second receiving space, wherein the body portion of the first resilient element abuts against the second abutting portion, and the head portion of the first resilient element is disposed inside the first circumferential wall to hermetically seal the first channel, wherein the first abutting portion abuts against the second end wall, and the at least second through hole of the second protruding portion is received in the second channel, allowing the first passage and the second passage to be in communication with the second channel.

2. The safety medical connector of claim 1, further comprising a sealing element attached to the second end wall, being abutted against by the first abutting portion, and having a third through hole penetrable by the second protruding portion.

3. The safety medical connector of claim 2, wherein the sealing element has two opposing parallel surfaces, one said surface attached to an inner wall surface of the second end wall, and another said surface being abutted against by the first abutting portion.

4. The safety medical connector of claim 1, wherein the peripheral wall has at least a slit, and the first fixing portion of the second resilient element fits around an outer wall surface of the peripheral wall, allowing the connecting portion to be penetratingly disposed at the slit.

5. The safety medical connector of claim 1, wherein the first inner pipe has two opposing first abutting portions, and the second inner pipe has two opposing second abutting portions.

6. The safety medical connector of claim 1, wherein the free end of the first protruding portion is tapered and has a first lateral surface, the first through hole disposed on the first lateral surface.

7. The safety medical connector of claim 1, wherein the free end of the second protruding portion is tapered and has a second lateral surface, the second through hole disposed on the second lateral surface.

8. The safety medical connector of claim 1, wherein a neck portion is disposed at a junction of the head portion and the body portion of the first resilient element, and a pressing portion is disposed at a junction of the first end wall and the first circumferential wall, the pressing portion pressing against the neck portion.

9. The safety medical connector of claim 1, wherein a positioning notch is disposed at the body portion of the first resilient element, and a flange is disposed at the second abutting portion, the flange engaged with the positioning notch.

10. The safety medical connector of claim 1, wherein a resilient ring is disposed between the fitting portion of the first inner pipe and the trunk portion of the second inner pipe.

* * * * *